United States Patent [19]

Lindsay

[11] Patent Number: 5,149,318
[45] Date of Patent: Sep. 22, 1992

[54] QUICK-CHANGEOVER BLOOD HANDLING APPARATUS

[75] Inventor: Erin J. Lindsay, Dexter, Mich.

[73] Assignee: Minnesota Mining and Manufacturing Company, Saint Paul, Minn.

[21] Appl. No.: 493,286

[22] Filed: Mar. 14, 1990

[51] Int. Cl.⁵ ............................................. B01D 19/02
[52] U.S. Cl. ....................................... 604/4; 604/319; 604/405; 604/406; 128/DIG. 3
[58] Field of Search ........................................ 604/4–6, 604/317–319, 403, 405, 406, 248, 249, 905; 128/DIG. 3; 137/614

[56] References Cited

U.S. PATENT DOCUMENTS

| | | |
|---|---|---|
| 617,591 | 1/1899 | Miller et al. |
| 978,029 | 12/1910 | Kell |
| 981,866 | 1/1911 | Lockhart |
| 1,871,421 | 8/1932 | Muhlhauser et al. |
| 1,885,321 | 11/1932 | Benn |
| 3,678,959 | 7/1972 | Liposky ................... 137/625.11 |
| 4,064,909 | 12/1977 | Neward ................... 137/625.48 |
| 4,432,760 | 2/1984 | Mittleman et al. ................... 604/405 |
| 4,432,465 | 2/1984 | Bellotti et al. ................... 604/283 |
| 4,440,723 | 4/1984 | Gordon ................... 128/DIG. 3 |
| 4,568,345 | 2/1986 | Keilman et al. ................... 604/403 |
| 4,576,199 | 3/1986 | Svensson et al. ................... 137/614.04 |
| 4,617,012 | 10/1986 | Vaillancourt ................... 604/29 |
| 4,664,682 | 5/1987 | Monzen ................... 604/406 |
| 4,708,370 | 11/1987 | Todd ................... 285/12 |
| 4,822,341 | 4/1989 | Colone ................... 604/175 |
| 4,846,800 | 7/1989 | Ouriel et al. ................... 604/319 X |
| 4,904,001 | 2/1990 | Sasa et al. ................... 285/316 |
| 4,909,780 | 3/1990 | Ouriel et al. ................... 604/4 |

FOREIGN PATENT DOCUMENTS

| | | |
|---|---|---|
| 0312101 | 4/1989 | European Pat. Off. |
| 2135890 | 9/1984 | United Kingdom |

OTHER PUBLICATIONS

Bentley ®, BCR-3538, Cardiotomy Autotransfusion Reservoir with Filter (CATR ™), Oct. 28, 1985.
Pleur-evac ®, Adult-Pediatric Single Use Chest Drainage Unit Dry Suction Control, Instructions for Use, 1988.
Baxter, Bentley ®, CATR ™ Cardiotomy Autotransfusion Reservoir System, Instructions for Use, Feb. 3, 1988.
Bard ®, William Harvey ® H–4700 Series Cardiotomy Reservoir, Directions for Use, revised Jun. 1989.
The Thora-Klex ® Chest Drainage Systems.
Sarns/3M, SMO/IR Training Manual, Jan. 13, 1989.
Gish Stat-Vac (SVP) 400/450 Pak, Directions for Use.
Foster, A Review of and Current Trends in Blood Conservation.
Sarns ® Membrane Oxygenator, 1988.
Sarns ® Membrane Oxygenator, Compendium of in vitro, ex vivo, and in vivo Performance Characteristics, Aug. 1987.

(List continued on next page.)

Primary Examiner—Robert A. Hafer
Assistant Examiner—Kerry Owens
Attorney, Agent, or Firm—Armstrong, Teasdale, Schlafly & Davis

[57] ABSTRACT

An apparatus for handling a patient's blood during a medical procedure which is convertible for use after the procedure for at least one further use. The apparatus comprises a reservoir having a port comprising at least one opening. A primary device, alignable with the port for adapting the reservoir for use during the procedure. The apparatus further comprises one or more secondary devices each alignable with the port means for adapting the reservoir for one or more further uses after the procedure. The primary device and the secondary devices are slidably mounted on the apparatus between tracks, with the primary device initially aligned with the port to allow the reservoir to be used during the medical procedure. The tracks allow the primary device to be moved out of alignment with the port and allow at least one of the secondary devices to be moved into alignment with the port so that the reservoir can be used after the medical procedure.

42 Claims, 5 Drawing Sheets

OTHER PUBLICATIONS

Boldt et al., "Blood conservation in cardiac operations", The Journal of Thoracic and Cardiovascular Surgery, vol. 97, No. 6, Jun. 1989.

Butler, "Current trends in autologous transfusion", RN, Nov. 1989.

HSVRF Hardshell Venous Reservoir with Interal Cardiotomy Filter, Instructions for Use, 1987.

Thora-Klex ® Autotransfusion Kit, Instructions for Use, revised Mar. 1988.

Autotransfusion. Faster, safer and more cost-effective. Atrium.

D 701-D 702 Masterflo Infant and Paediatric Hollow Fibre Oxygenators.

Hemodynamic Duo.

Introducing the Gish CAP-35 TM cardiotomy reservoir and pleural drainage unit with the capacity for autotransfusion.

For you, the Gish CAP-35 TM works . . . .

Gish-ATR TM Blood Recovery/Autotransfusion System, Directions for Use.

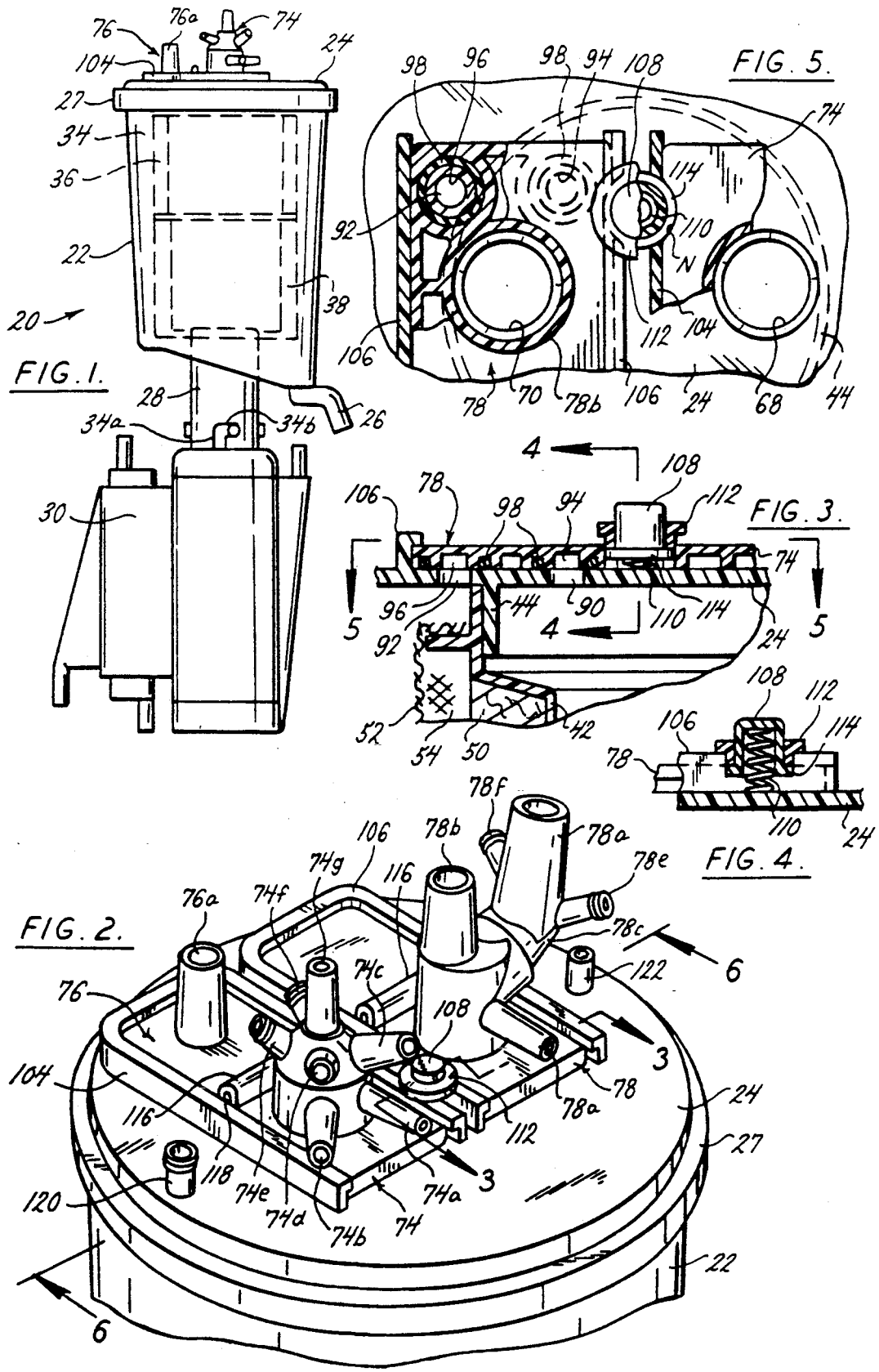

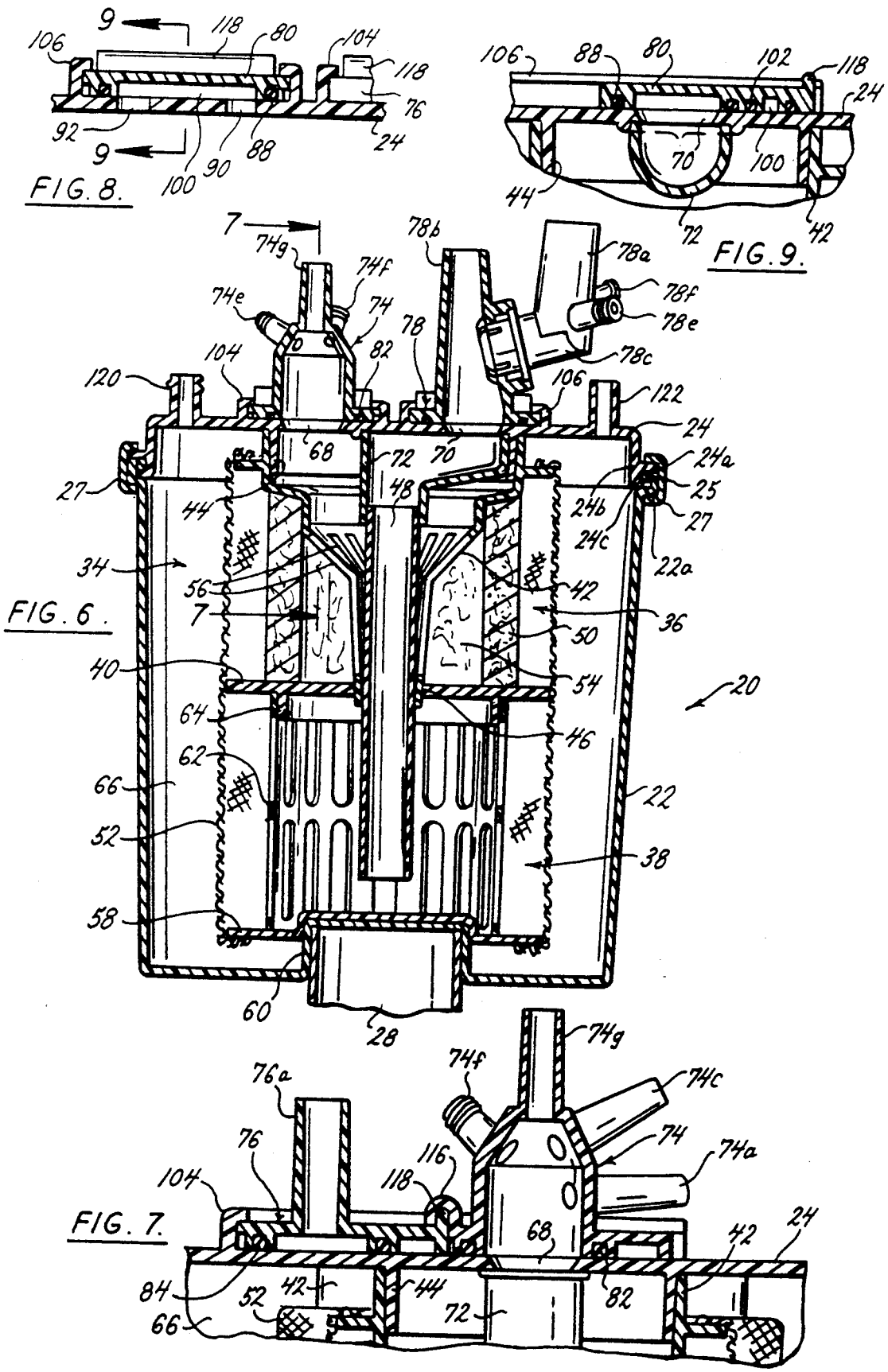

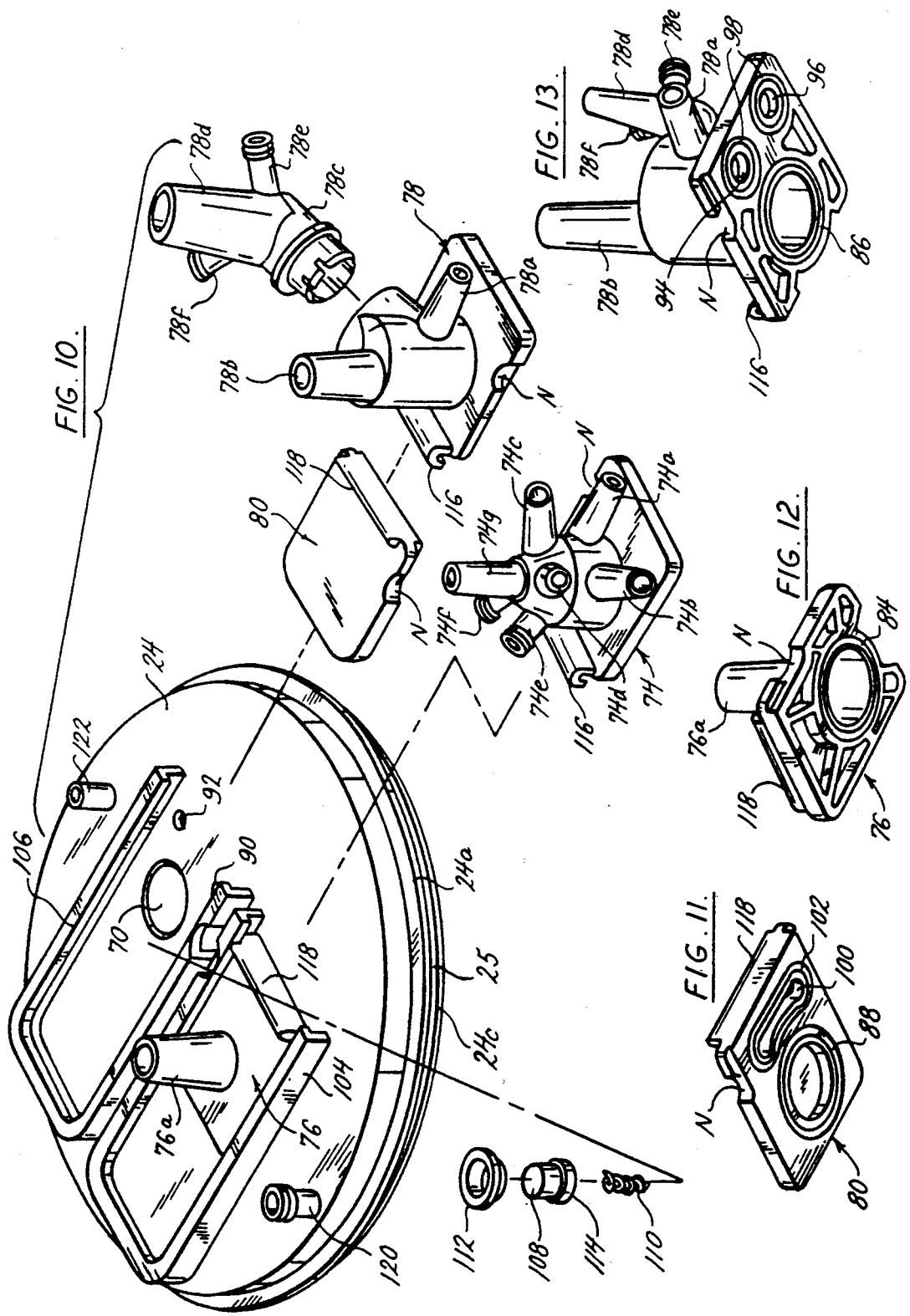

QUICK-CHANGEOVER BLOOD HANDLING APPARATUS

BACKGROUND OF THE INVENTION

This invention relates to a quick-changeover blood handling apparatus, and in particular to an apparatus for handling a patient's blood during a medical procedure which is convertible for use in blood collection after the procedure.

There are instances where one blood handling device would be used for a patient during a medical procedure, and another blood handling or collecting device would be needed for post-procedure care. For example, in the case of heart surgery, a blood reservoir is used as part of the blood recovery and oxygenation system. After the procedure, a separate autotransfusion reservoir might be used to collect the patient's blood from the surgical wound for reuse, and/or another reservoir might simply be used to collect blood drained from the surgical wound for disposal. Several "convertible" devices are available that can be used both as a blood reservoir during surgery and a pleural drainage unit after surgery. These devices provide several advantages: they eliminate the need for dedicated pleural drainage devices; they minimize the amount of disposable equipment that is used (and must be disposed of); they are more economical; and they reduce staff-time associated with setting up multiple devices. Moreover, many of these devices allow for autotransfusion of the collected blood, reducing risk to the patient and reducing the demand for blood products.

However, to varying degrees these devices have also suffered from one significant draw-back: the conversion of these devices from use as a surgical blood reservoir to a drainage unit or to an autotransfusion device is time consuming and complex. Many of these devices come with pages of detailed instructions that the nursing staff is expected to follow to properly disconnect and cap the numerous connectors required for use as a surgical blood reservoir. Some of these devices even require special kits, with further instructions and additional parts that must be set aside and later installed, to make the conversion. This increases the pressure on the nursing staff to quickly and accurately make the conversion. Furthermore, each tube connection that must be undone and capped increases the chance of blood splattering the medical staff, with the attendant risk of spreading disease, such as hepatitis and AIDS.

SUMMARY OF THE INVENTION

The present invention provides an apparatus for handling a patient's blood during a medical procedure which can be quickly and easily converted for use in blood collection after the procedure. The present invention eliminates most of the detailed disconnecting and capping steps required by the previously available convertible apparatus by providing an apparatus with connection devices or blocks that can simply be removed after use in one mode and replaced by new connection devices or blocks specially adapted for use in the new mode. All the parts required for use in both modes are provided on the apparatus. Conversion is a matter of sliding the proper devices into their operative positions.

Generally, the apparatus of the present invention comprises a reservoir having a port means therein comprising at least one opening. The apparatus also includes a primary device, alignable with the port means, for adapting the reservoir for use during a medical procedure, and one or more secondary devices, each alignable with the port means, for adapting the reservoir for one or more further uses after the medical procedure. The apparatus further includes means for mounting the primary device and the secondary devices on the reservoir with the primary device initially aligned with the port means to allow the reservoir to be used during the medical procedure. The mounting means allows the primary device to be moved out of alignment with the port means and allows at least one of the secondary devices to be moved into alignment with the port means to allow the reservoir to be used after the medical procedure.

In the first preferred embodiment of the invention there are first and second port means. There are first and second devices each alignable with the first port means, and means for mounting the first and second devices adjacent the first port means. There are also third and fourth devices each alignable with the second port means, and a means for mounting the third and fourth devices adjacent the second port means. The first and third devices are initially aligned with their respective port means for use during the medical procedure. After the procedure, the first and third devices are moved out of alignment with their respective port means and the second and forth devices are moved into alignment with their respective port means to adapt the apparatus for its post-procedure use.

In the second preferred embodiment there is a single port means, first and second devices, and means for mounting the first and second devices adjacent the port means. The first device is initially aligned with the port means for use during the procedure. After the procedure, the first device is moved out of alignment with port means and the second device is moved into alignment with the port means to adapt the apparatus for its post-procedure use.

In the third preferred embodiment there is one port means, a primary device and at least two secondary devices. Mounting means mounts the devices adjacent the port means. The primary device is initially aligned with the port means. After the procedure the primary device is moved out of alignment with the port means, and one of the secondary devices is moved into alignment with the port means to adapt the apparatus for its post-procedure use.

The devices of the first, second, and third preferred embodiments can be variously constructed. For example they may include connectors for making connections with their respective port means. The port means can include multiple openings and at least some of the devices can include multiple connectors for making separate connections with the separate openings of the port means. The reservoir can comprise separate chambers, and the port means can include vent openings communicating with each of the chambers, in which case some of the devices can comprise means for closing the vent openings and others of the device can include means for connecting the vent openings.

The mounting means in the first, second, and third preferred embodiments preferably comprises means for slidably mounting their respective devices, and more preferably a pair of tracks between which the devices are mounted. In the first and second preferred embodiments, the mounting means may be a generally U-shaped track, so that movement of the devices in one direction is restricted. In the third preferred embodiment the mounting means may be two parallel, open ended tracks so that the devices can move in two directions. Some means may be provided to releasably lock the devices in position, to prevent their inadvertent movement.

The present invention thus provides an apparatus that can be used during a medical procedure, but which can be quickly and conveniently converted for post-procedure use. Connections are made to a first set of devices so that the apparatus can be used during the medical procedure. After the procedure, rather than making numerous disconnections, capping connectors, and closing valves, the devices of the first set are moved from their operative positions, and may even be removed from the apparatus. A second set of devices, specially adapted for the post procedure use, take the place of the first set of devices. All of the parts needed for the conversion are provided on the apparatus, and conversion is simply a matter of sliding parts on the apparatus. The conversion process is greatly simplified and expedited, and the chance for error is significantly reduced. Thus the advantages of a convertible device are realized without the difficulties previously encountered.

These and other advantages will be in part apparent and in part pointed out hereinafter.

BRIEF DESCRIPTION OF THE DRAWINGS

FIG. 1 is a side elevation view of a first embodiment of the present invention in the form of a cardiotomy reservoir;

FIG. 2 is a perspective view of the first embodiment;

FIG. 3 is a partial cross-sectional view of the first embodiment, taken along the plane of line 3—3 in FIG. 2;

FIG. 4 is a partial cross-sectional view of the first embodiment, taken along the plane of line 4—4 in FIG. 3;

FIG. 5 is a partial cross-sectional view of the first embodiment, taken along the plane of line 5—5 in FIG. 3;

FIG. 6 is a cross-sectional view of the first embodiment, taken along the plane of line 6—6 in FIG. 2;

FIG. 7 is a partial cross-sectional view of the first embodiment, taken along the plane of line 7—7 in FIG. 6;

FIG. 8 is a partial cross-sectional view of the first embodiment, after the fourth device has been moved into alignment with the port means;

FIG. 9 is a partial cross-sectional view of the first embodiment, taken along the plane of line 9—9 in FIG. 8, after the fourth device has been moved into alignment with the port means;

FIG. 10 is an exploded perspective view of the first embodiment;

FIG. 11 is a perspective view from below of the fourth device of the first embodiment;

FIG. 12 is a perspective view from below of the second device of the first embodiment;

FIG. 13 is a perspective view from below of the third device of the first embodiment;

Corresponding reference numerals indicate corresponding parts throughout the several views of the drawings.

DETAILED DESCRIPTION OF THE PREFERRED EMBODIMENTS

Figure 14:
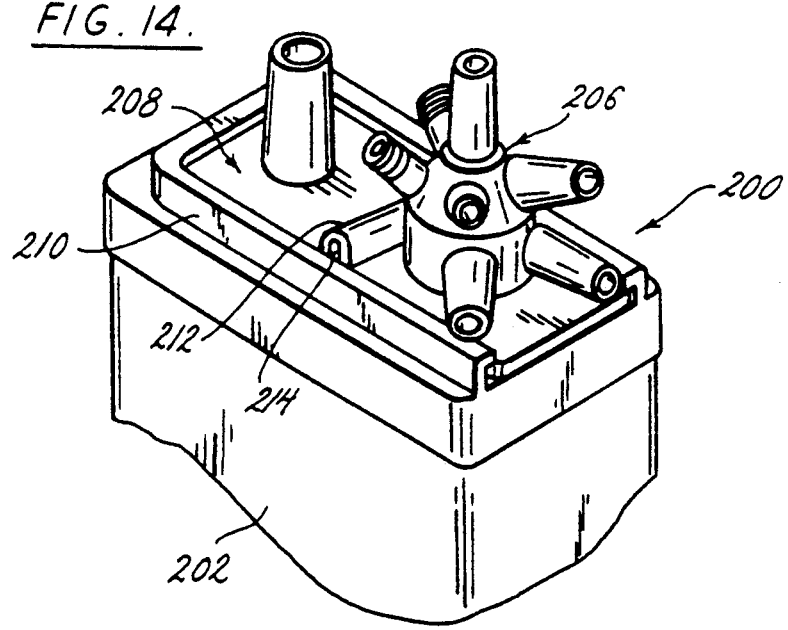
FIG. 14 is a perspective view of a second embodiment of the present invention.

A first embodiment of this invention in the form of a surgical blood apparatus is indicated generally as 20 in FIG. 1. The surgical blood apparatus 20 is adapted for use as part of a blood recovery and oxygenation system of the type used during cardiac surgery. However, according to the principles of this invention the apparatus 20 is also convertible for use in blood collection after the surgical procedure. Although described with respect to surgical blood apparatus 20, this invention is not so limited, and could be applied to other blood-handling apparatus used during a medical procedure.

The surgical blood apparatus 20 comprises a reservoir 22 having an open top closed by a lid 24. As best shown in FIG. 6, the reservoir 22 and the lid 24 are constructed to permit the lid 24 to rotate with respect to reservoir 22, while maintaining a seal. The lid 24 has a rim 24a that rests on the top edge of the reservoir 22. A portion 24b of the lid extends into the reservoir 22, and has an annular groove 24c that contains an O-ring as for sealingly engaging the interior wall of the reservoir, while permitting relative rotation. A retaining ring 27, having a channel-shaped cross-section, engages both the top of the lip 24a and a shoulder 22a in the reservoir 22, to retain the lid 24 in the reservoir. This mounting allows the lid, and all the connectors thereon to swivel for more convenient handling of the apparatus 20. It will be appreciated that the interior of the apparatus 20 is constructed to allow for this swivel-action. The reservoir 22 has an outlet 26 in its lowermost portion. As is well known in the art, during cardiac surgery the outlet 26 is connected to either a venous reservoir or to a blood pump if the surgical blood apparatus 20 is used as a venous reservoir as well as a cardiotomy combination. After surgery the outlet 26 may be connected to a blood pump to return collected blood to the patient. A hollow cylinder 28 projects from the bottom of the reservoir 22 for mounting the reservoir on to an oxygenator 30. The cylinder 28 may be provided with L-shaped slots 32 by which the apparatus may be releasably secured to the oxygenator 30, with a bayonet-style connection, as described in more detail below.

As is well known in this art, a blood filter/defoamer unit 34 is mounted inside the reservoir 22. As best shown in FIG. 6, the unit 34 comprises an upper blood filtration section 36 and a lower blood defoaming section 38, separated by a generally planar horizontal separating plate 40. The unit 34 is constructed so that blood can be separately provided to the filtration section 36 and to the defoaming section 38.

The blood filtration section 36 comprises a generally funnel-shaped member 42 for receiving blood to be filtered. The mouth of the funnel-shaped member 42 is adapted to fit around an annular support 44 depending from the lower surface of the lid 24. The lower end of the funnel-shaped member 42 is supported in a hole 46 in the center of the plate 40. The member 42 is sealed with the plate 40 to prevent blood from passing from the filtration section 36 to the defoaming section 38. A tube 48 extends axially through the funnel-shaped member 42 to the defoaming section 38, and is sealed with the lower end of the funnel-shaped member 42 to prevent blood from passing from the funnel-shaped member 42 into the defoaming section 38.

The funnel-shaped member 42 is surrounded by a generally cylindrical filter member 50. The top of the filter member 50 abuts the funnel-shaped member 42 and the bottom of the filter member 50 abuts the plate 40, defining a filtration chamber 54 between the filter member 50 and the funnel-shaped member 42. The body of the funnel-shaped member 42 has a plurality of radially extending slots 56 therein so that blood provided to the funnel-shaped member passes to the filtration chamber 54. The blood can then pass through the filtration member 50, which removes clots and debris, etc. There is a defoamer mesh sock 52 that extends the entire height of unit 34.

The defoamer section 38 comprises a base plate 58 supported on a cylindrical projection 60 in the bottom of the reservoir 22. A substantially rigid, perforated cylindrical defoamer retainer 62 is supported on the base plate 58 and extends to the plate 40. The upper end of the defoamer retainer 62 is adapted to fit around an annular support 64 depending from the underside of the plate 40. Blood passes through the tube 48 into the defoamer section 38. The blood can then pass through the defoamer retainer 62, whereby it is defoamed when it passes through the defoamer mesh sock 52. The entire unit 34 is surrounded by a woven sock 66.

As noted above, blood can be separately provided to the filtration section 36 or to the defoaming section 38. As shown in FIG. 6, the lid 24 includes a first port means, comprising at least one opening 68, aligned with the open mouth of the funnel-shaped member 42. Thus, blood that passes through opening 68 of the first port means is provided to the filtration section 36. Blood that is recovered in surgery from suctioning the surgical area must be filtered before it can be returned to the blood stream; this blood is provided to the first port means. The lid 24 also includes a second port means, comprising at least one opening 70. The opening 70 is aligned with a collector 72, which discharges to the tube 48. Thus, blood that passes through the opening 70 of the second port means is provided to the defoamer section 38. Blood that is collected directly from the patient's venous system generally does not have to be filtered. However this blood does tend to froth and must be defoamed before it can be returned to the blood stream; this blood is provided to the second port means.

According to the first embodiment of this invention, the apparatus 20 includes a first device 74, alignable with the first port means, for adapting the apparatus 20 for use during surgery, and a second device 76 alignable with the first port means, for adapting the apparatus for use after surgery. The apparatus 20 further includes first mounting means for mounting the first and second devices 74 and 76 on the lid 24 of the reservoir 22 with the first device 74 initially aligned with the first port means to allow the reservoir to be used during surgery. The first mounting means allows the first device 74 to be moved out of alignment with the first port means, and allows the second device 76 to be moved into alignment with the first port means so that the apparatus 20 can be used after surgery. Specifically, the first device 74 is adapted to facilitate the delivery of blood, collected during surgery and needing filtration, to the first port means. The second device 76 is adapted to facilitate the delivery of blood collected after surgery and needing filtration, to the first port means.

The apparatus 20 further includes a third device 78 alignable with the second port means for adapting the apparatus 20 for use during surgery, and a fourth device 80 alignable with the second port means for adapting the apparatus 20 for use after surgery. The apparatus 20 further includes second mounting means for mounting the third and fourth devices 78 and 80 on the lid 24 of the reservoir 22 with the first device 78 initially aligned with the second port means to allow the reservoir to be used during surgery. The second mounting means allows the third device 78 to be moved out of alignment with the second port means and allows the fourth device 80 to be moved into alignment with the second port means, so that the apparatus 20 can be used after surgery. Specifically, the third device 78 is adapted to facilitate the delivery of venous blood, collected during surgery and needing defoaming, to the second port means. The fourth device 80 is adapted to close the second port means after surgery because venous blood is no longer returned to the reservoir after surgery is completed.

The first device 74, which is shown best in FIGS. 2 and 6, comprises a plurality of connectors 74a, 74b, 74c, 74d, 74e, 74f, and 74g. Each of these connectors is adapted to make a connection with equipment used during surgery. For example, connectors 74a, 74b, 74c, and 74d are adapted to connect to surgical field suction devices in order to scavenge lost blood from the wound area; connector 74e is adapted to connect to a luer syringe in order to add drugs; connector 74f is adapted to connect to a luer syringe in order to sample the suctioned blood; and connector 74g is adapted to connect to a prime solution container in order to prime the filter portion of the reservoir.

In this first preferred embodiment, all of the connectors 74a–74g communicate with each other, and with the single opening 68 of the first port means. A gasket 82 is mounted in an annular recess in the bottom of the first device 74 to seal with the first port means when the first device 74 is aligned therewith. (Alternately, the gasket 82 could be mounted in a recess in the lid 24, adjacent port means.) However, the first port means could comprise more than one opening. In this case, not all of the connectors of the first device 74 would have to communicate, and thus first device 74 would permit separate connections to be made with the reservoir 22. Of course, separate gaskets 82 could be provided on the first device (or on the lid 24) to seal each connection.

The second device 76, which is shown best in FIGS. 2, 10, and 12, comprises a single connector 76a. The connector 76a is adapted to make a connection used after surgery, for example, to a chest drainage tube to collect the blood from the surgical wound. A gasket 84 is mounted in an annular recess in the bottom of the second device 76 to form a seal with the first port means when the second device 76 is aligned therewith. (However, if gasket 82 is mounted in lid 24, no gasket 84 is needed in device 76.)

The third device 78, which is shown best in FIGS. 2, 10, and 13, comprises a plurality of connectors 78a and 78b, and a swivel member 78c pivotally mounted in an opening in third device 78, and having three additional connectors 78d, 78e, and 78f. Each of these connectors 78a, 78b, 78d, 78e, and 78f is adapted to make a connection with equipment used during surgery. For example, connector 78a is adapted to connect to the oxygenator in order to allow blood recirculation; connector 78b is adapted to connect to an optional cardiotomy reservoir in order to add additional suctioned blood; connector 78d is adapted to connect to the venous return tube from the patient in order to oxygenate the blood; connector 78e is adapted to connect to a temperature probe in order to monitor venous blood temperature; and connector 78f is adapted to connect to a luer syringe for venous blood sampling.

In this preferred embodiment, all these connectors communicate with each other and with the opening 70 of the second port means. A gasket 86 is mounted in an annular recess in the bottom of the third device to seal with the second port means when the third device 78 is aligned therewith. (Gasket 86 could alternately be mounted in a recess in lid 24 adjacent to opening 70 of second port means.) However, the second port means could comprise more than one opening. In this case, not all of the connectors of the third device would have to communicate, and thus third device 78 would permit separate connections to be made with the reservoir 22. Of course, separate gaskets 86 could be provided on the third device (or on the lid 24) to seal each connection.

The fourth device 80, which is best shown in FIGS. 10 and 11, has no connectors. The fourth device 80 serves to close the second port means after surgery. A gasket 88 is mounted in an annular recess in the bottom of the fourth device 80, to form a seal with the second port means when the fourth device is aligned therewith. (However, if gasket 86 is mounted in lid 24, no gasket 88 is needed in device 80.)

As discussed above, the reservoir 22 is in fact divided into several sections or chambers which during use of the apparatus 20 can be at different pressures. For example one chamber could be considered to be inside the unit 34, and the other chamber could be considered to be outside the unit 34. At least one of the first and second port means, and in this first preferred embodiment the second port means, can comprise vent holes 90 and 92, each in communication with a different chamber (for example, one communicates with the filtration section 36 and the other communicates with the interior of the reservoir outside the filtration section 36 or one communicates with the defoaming section 38 and the other communicates with the interior of the reservoir outside the defoaming section). Sometimes it may be desirable that these chambers be isolated, but at other times it may be desirable that the chambers communicate. Thus, one of the devices may include means for sealing each of the vent holes 90 and 92, and another of the devices may include means for allowing these vent holes to communicate. In this preferred embodiment, as best shown in FIG. 13, the third device 78 has two recesses 94 and 96 in its underside surface, each of which is surrounded by a gasket 98 held in an annular recess in the bottom surface of the third device 78. When the third device 78 is aligned with the second port means, the recesses 94 and 96 align with the vent holes 90 and 92 to close and isolate the vent holes. As best shown in FIG. 11, the fourth device 80 has a large, kidney-shaped recess 100 therein, surrounded by a gasket 102. When the fourth device 80 is aligned with the second port means, the recess 100 is aligned with the vent holes 90 and 92 and allows them to communicate, for example to equalize the pressure in the two chambers with which the vent holes communicate. In this first preferred embodiment the vent holes communicate with the defoamer section 38 and the interior of the reservoir 22, respectively. These are isolated by the third device 78 during surgery, and connected by the fourth device 80 after surgery.

The first, second, third, and fourth devices, 74, 76, 78, and 80, respectively, are slidably mounted on the lid 24 of the reservoir 22. The first mounting means comprises opposing, parallel tracks between which the first and second devices 74 and 76 are slidably mounted, and the second mounting means comprises opposing, parallel tracks between which the third and fourth devices 78 and 80 are slidably mounted. In this first preferred embodiment, the first mounting means comprises a first generally U-shaped track 104, having a closed bottom end, two generally parallel legs, and an open top end. As best shown in FIG. 2, initially the second device 76 is positioned between the legs of the "U" adjacent the closed end, and the first device 74 is positioned between the legs of the "U" adjacent the open end. The second mounting means comprises a second generally U-shaped track 106, having a closed bottom end, two generally parallel legs, and an open top end. As best shown in FIG. 2, initially the fourth device 80 is positioned between the legs of the "U" adjacent the closed end, and the third device 78 is positioned between the legs of the "U" adjacent the open end. In cross-section the tracks 104 and 106 have a generally inverted "L" shape, with a vertically extending sidewall for retaining the devices between them, and a horizontally extending rim for retaining the devices against the lid 24. The first and second U-shaped tracks 104 and 106 are preferably positioned side-by-side on the reservoir.

The apparatus 20 preferably also comprises means for releasably locking the devices in position when each is aligned with its respective port means. In this first preferred embodiment, the releasable locking means comprises a detent or button 108, operable between an extended position in which the button 108 engages the device aligned with the port means, and a depressed position in which the button 108 does not engage the device aligned with the port means. The button 108 is preferably mounted in the space between the tracks 104 and 106 on the lid 24 thus, a single button 108 can simultaneously secure two devices. The tracks 104 and 106 have a cut out so that the button 108 can engage the devices mounted in the tracks. The button 108 is resiliently biased to its extended position by a spring 110. The button is retained in the recess by an annular bezel 112 which engages a projecting rim 114 on the body of the button 108. Each of the devices 74, 76, 78, and 80 may have a notch N therein to engage the button.

The apparatus 20 preferably further comprises means for releasably interlocking the first and second devices 74 and 76 so that the first and second devices move with each other in the track 104, and means for releasably interlocking the third and fourth devices 78 and 80 so that the third and fourth devices move with each other in the track 106. This simplifies the conversion of the apparatus 20, and prevents the port means from becoming uncovered. In this preferred embodiment, the first and third devices 74 and 78 have an inverted channel 116 on their respective rear edges that is adapted to engage an upstanding lip 118 on the front edges of the second and fourth blocks 76 and 80, respectively. Thus as the first device 74 is moved out of alignment with the first port means, the second device 76 is moved into alignment with the first port means. Since the first device 74 is no longer constrained in the track 104, it can be lifted and simply removed. Likewise, as the third device 78 is moved out of alignment with the second port means, the fourth device 80 is moved into alignment with the second port means. Since the third device 78 is no longer constrained in the track 106, it can be lifted and simply removed. The lid 24 of the reservoir includes two other connectors 120 and 122. Connector 120 is adapted for connection to a priming fluid container in order to prime the non-filtered, outer reservoir chamber or vent or wall suction after surgery, and connector 122 is adapted for limiting wall vacuum with a relief valve.

A second embodiment of this invention, indicated generally as 200, is shown in perspective in FIG. 14. The apparatus 200 is adapted for handling a patient's blood during a medical procedure and is convertible for use in blood collection after the procedure. The apparatus 200 is similar in construction to apparatus 20, however, instead of four devices, there are only two devices mounted on the apparatus. The apparatus 200 comprises a reservoir 202, having a port means comprising at least one opening therein. The apparatus further comprises a first device 206, alignable with the port means, for adapting the reservoir for use during the procedure, and a second device 208, alignable with the port means, for adapting the reservoir for use after the procedure. The apparatus has a mounting means for mounting the first and second devices 206 and 208 on the reservoir 202 with the first device initially aligned with the port means to allow the reservoir to be used during the medical procedure. The mounting means allows the first device 206 to be moved out of alignment with the port means and allows the second device 208 to be moved into alignment with the port means to allow the reservoir to be used after the medical procedure.

The first device 206 is similar in construction to first device 24, described above, and preferably comprises at least one connector that communicates with the opening when the first device is aligned with the port means. The connector allows a connection to be made with the reservoir so that the apparatus 200 can be used during the medical procedure. The second device 208 is similar in construction to the second device 76, described above, and likewise comprises at least one connector that communicates with the opening when the second device is aligned with the port means. The connector allows a connection to be made with the reservoir to use the apparatus 200 after the medical procedure. The port means may comprise a plurality of openings, and at least one of the devices may comprise a plurality of connectors, each communicating with one of openings when its respective device is aligned with the port means, to allow separate connections to be made to the reservoir 202.

As described above with respect to the first embodiment, the reservoir 202 may be divided into more than one chamber. In such a case, the port means may comprise a vent hole communicating with each chamber. One of the first and second devices 206 and 208 could then comprise means for closing the vent holes, and the other of the first and second devices 206 and 208 comprise means for connecting the vent holes (for example to equalize the pressure between the chambers).

The first and second devices 206 and 208 are preferably slidably mounted on the reservoir 202. The mounting means preferably comprises opposing, parallel tracks between which the first and second devices are slidably mounted. As described above with respect to the first embodiment, the mounting means preferably comprises a generally U-shaped track 210 having a closed end, two generally parallel legs, and an open end. The second device 208 is positioned between the legs of the "U" adjacent the closed end, and the first device 206 is positioned between the legs of the "U" adjacent the open end.

The apparatus may further comprise means for releasably locking the first and second devices in position when each is aligned with the port means. This means may be like the releasable locking means of the first embodiment, comprising a detent or push button like button 108 operable between an extended position in which the push button engages the first and second devices, and a depressed position in which the push button does not engage the first and second devices.

Also like the first embodiment, the first and second devices 206 and 208 may be releasably connected together so that they move together. The first device 206 may have a downwardly facing channel 212 which engages an upwardly projecting lip 214 on the second device 208.

Figure 15:
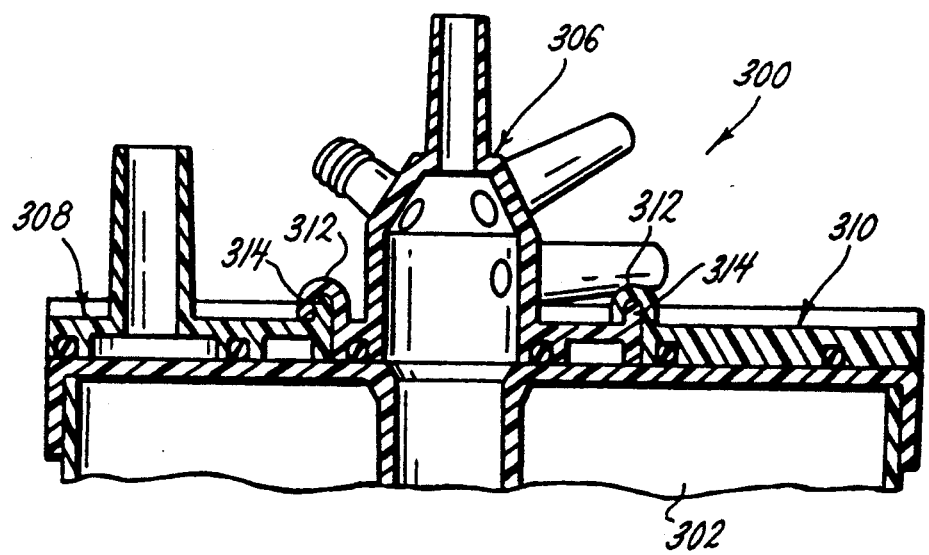
FIG. 15 is a partial cross-sectional view of a third embodiment of the present invention.

A third embodiment of this invention indicated generally as 300 is shown in cross section in FIG. 15. The apparatus 300 is adapted for use in handling a patient's blood during a medical procedure and is convertible for use after the procedure for at least one further use. The apparatus 300 comprises a reservoir 302, having port means therein comprising at least one opening 304. The apparatus further comprises a primary device 306, alignable with the port means, for adapting the reservoir 302 for use during the procedure, and one or more secondary devices each alignable with the port means for adapting the reservoir for one or more further uses after the procedure. In this third preferred embodiment there are two such secondary devices 308 and 310. The primary device 306 and the secondary devices 308 and 310 may be similar in construction to the devices described in the first and second embodiments. The apparatus 300 includes means for mounting the primary device and the secondary devices on the reservoir with the primary device 306 initially aligned with the port means to allow the reservoir to be used during the medical procedure. The mounting means allows the primary device 306 to be moved out of alignment with the port means and allows at least one of the secondary devices 308, 310, to be moved into alignment with the port means to allow the apparatus to be used after the medical procedure.

The mounting means preferably comprises a pair of generally parallel tracks between which the primary and secondary devices 306, 308, and 310 are slidably mounted. The tracks are preferably open at both ends so that the primary and second devices can slide between the tracks in either direction.

In this third preferred embodiment the secondary devices 208 and 210 are preferably mounted one on either side of the primary device (as shown). However, the secondary devices 208 and 210 could be mounted on the same side of the primary device 200, if desired. In either event, the primary and secondary devices are preferably releasably secured together so that they move together. For example, the devices may be provided with interlocking downwardly facing channels 312 and upwardly projecting lips 314.

The blood reservoir 20 (or any of the apparatus of this invention) may be mounted with a bayonet-style mounting consisting of a plurality of generally L-shaped slots 32 for receiving and engaging pins 33 projecting from the device, e.g. blood oxygenator 30, on which the reservoir is mounted. The L-shaped slots 32 have an outer reach 32a extending generally axially of the apparatus, and an inner reach 32b extending generally circumferentially of the apparatus. The apparatus is moved downwardly over the pins 33, so that the pins 33 penetrate into the outer reaches 32a of the slots. The apparatus is then rotated relative to the pins so that pins penetrate into the inner reaches 32b of the slots.

Figure 16:
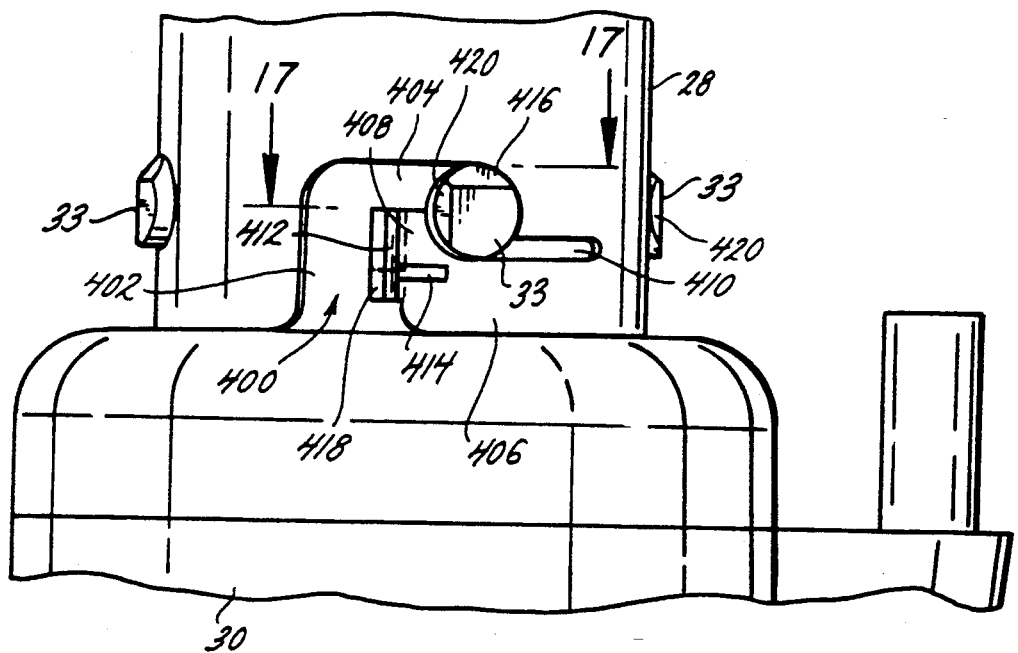
FIG. 16 is a side elevation view of a locking slot for a bayonet mount that can be used with the reservoirs of this invention.
Figure 17:
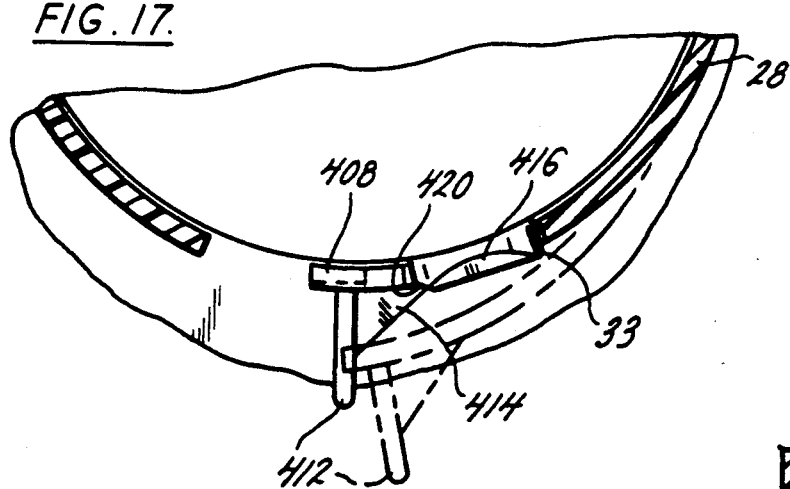
FIG. 17 is a partial cross-sectional view of the locking slot taken along the plane of line 17—17 in FIG. 16.
Figure 18:
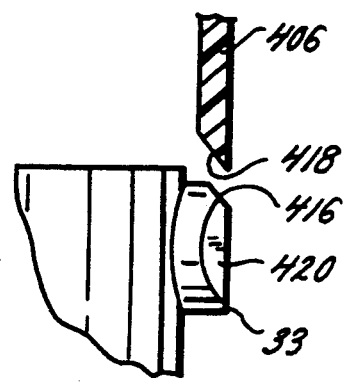
FIG. 18 is a partial side elevation view showing the camming surfaces on the pin and the tab.

One of these slots 32 is preferably constructed to releasably lock a pin in the inner reach of the slot to prevent the apparatus from being inadvertently dismounted. This releasably lockable slot, indicated generally as 400 in FIGS. 16–18, is likewise generally L-shaped, comprising an outer reach 402 and an inner reach 404. The slot defines a circumferentially extending tab 406. The end of this tab 406 has means, such as projection 408, for engaging and retaining the pin in the inner reach of the slot. The tab 406 is dimensioned and configured to be flexible so that the tab 406 can be flexed to pull projection 408 out of engagement with the pin. There is preferably an elongate slit 410, extending generally parallel to the tab from the end of the slot to facilitate the flexing of the tab. The end of the slit 410 is generally rounded to reduce stress concentration.

As best shown in FIG. 17, the end of the tab 406 has an outwardly projecting finger grip 412 for facilitating the flexing of the tab. A generally triangular reinforcing web 414 extends between the finger grip 412 and the tab 406.

As best shown in FIG. 18, either the upper portion 416 of the pins 33 or the lower edge 418 of the tab 406, or preferably both, are chamfered so that when the tab and the pin are urged together, the tab is cammed outwardly with respect to the pin so that the tab clear the pin. The reservoir is manipulated so that the pin is aligned with the inner portion of the slot. The tab "snaps" back providing a positive audible indication that the reservoir is properly seated and locked into place.

The pins 33 may also have chamfered side edges 420. The chamfered side edges 420 facilitate the disengagement of the projection 408 with the pin 33. Rather than a chamfered top edge and a chamfered side edge, the pins 33 could be made with the entire circumferential edge chamfered. Although only one locking device is provided on the reservoir, all of the pins have the chamfered edges so that the no particular orientation is required to secure the reservoir.

OPERATION

In operation, the apparatus 20 of the first embodiment is prepared for use by making the appropriate connections with the first device 74 to deliver suctioned blood collected during surgery to the filtering section 36 of the unit 34. Similarly, the appropriate connections are made with the third device 78 to deliver venous blood collected during surgery to the defoaming section 38 of the unit 34. The blood collected in the reservoir 22 is removed through outlet 26, and returned to the patient with a pump as is well known in this art. After the surgery is completed, rather than disconnecting all of the lines to the first and third devices 74 and 78, and capping their respective connectors, 74a, 74b, 74c, 74d, 74e, 74f, 74g, 78a, 78b, 78d, 78e, and 78f as had to be done with prior art devices, the push button 108 is simply pressed and the first device 74 is slid out of the track 104, which simultaneously brings the second device 76 into alignment with the first port means. Similarly, the third device 78 is slid out of the track 106 which simultaneously brings the fourth device 80 into alignment with the second port means.

With the second and fourth devices 76 and 80 aligned with the first and second port means, respectively, the apparatus 20 is now adapted for post-procedure use as a plueral drainage reservoir. A chest drainage tube can be connected to the connector 76a of the second device 76, so that blood suctioned from the surgical wound after surgery is filtered and stored in the reservoir 22. The fourth device 80 blocks second port means, which is not needed because all the post procedure blood should be filtered. The fourth block also equalizes the pressure within the chambers in the reservoir as described above.

In using the apparatus 200 of the second embodiment, the procedure is similar to that with respect to the first embodiment. Appropriate connections are made to the first device 200 to use the apparatus during the medical procedure. After the procedure, the connections don't have to be disconnected, nor do the connectors have to be capped. The first device 206 is slid out of the track 210 and the second device 208 is simultaneously brought into alignment with the port means. The apparatus 200 is thus adapted for its post procedure use. A connection is made with the second device 208 and the apparatus is ready for post procedure use.

In using the apparatus 300 of the third embodiment, the procedure is similar to that with respect to the first and second embodiments. Appropriate connections are made to the primary device 306 to use the apparatus 300 during the procedure. After the procedure, the connections may be disconnected for convenience, but the connectors do not have to be capped. The primary device 306 is simply slid to the left or to the right (as shown in FIG. 15) to bring the appropriate secondary device 308 or 310 into alignment with the port means. The third embodiment could even be arranged so that both the primary devices are on the same side. Thus a one or more secondary devices can be successively used so that the apparatus 300 is used in more than one subsequent procedure, or used in a subsequent procedure and closed.

As various changes could be made in the above constructions without departing from the scope of the invention, it is intended that all matter contained in the above description or shown in the accompanying drawings shall be interpreted as illustrative and not in a limiting sense.

What is claimed is:

1. An apparatus for handling a patient's blood during a medical procedure which is convertible for use after the procedure for at least one further use; the apparatus comprising:
   a reservoir;
   port means in the reservoir comprising at least one opening;
   a primary device alignable with the port means, to which connections can be made for adapting the reservoir for use during the medical procedure;
   at least one secondary device, separate from the primary device, alignable with the port means, to which connections can be made for adapting the reservoir for one or more further uses after the medical procedure; and means for mounting the primary device and the secondary device on the reservoir with the primary device initially aligned with the port means to allow the reservoir to be used during the medical procedure, the mounting means allowing the primary device to be moved out of alignment with the port means and removed from the reservoir and allowing a secondary device to be moved into alignment with the port means to allow the reservoir to be used after the medical procedure.

2. The apparatus according to claim 1 wherein there are at least two secondary devices.

3. The apparatus according to claim 2 wherein the means for mounting the primary and secondary devices comprises a pair of generally parallel tracks between which the primary and secondary devices are slidably mounted.

4. The apparatus according to claim 3 wherein there are at least two secondary devices, and wherein there is at least one secondary device on each side of the primary device.

5. The apparatus according to claim 3 wherein there are at least two secondary devices, and wherein all the secondary devices are located on the same side of the primary device.

6. The apparatus according to claim 3 wherein the primary and secondary devices are releasably connected together so that they move together.

7. An apparatus for handling a patient's blood during a medical procedure which is convertible for use in blood collection after the procedure, the apparatus comprising:

a reservoir;

port means in the reservoir comprising at least one opening;

a first device alignable with the port means to which connections can be made for adapting the reservoir for use during the medical procedure;

a second device, separate from the first device, alignable with the port means to which connections can be made for adapting the reservoir for use after the medical procedure; and mounting means for mounting the first and second devices on the reservoir with the first device initially aligned with the port means to allow the reservoir to be used during the medical procedure, the mounting means allowing the first device to be moved out of the alignment with the port means and removed from the reservoir, and allowing the second device to be moved into alignment with the port means to allow the reservoir to be used after the medical procedure.

8. The apparatus according to claim 7 wherein the first device comprises at least one connector device that communicates with the opening when the first device is aligned with the port means, by which a connection can be made with the reservoir to use the reservoir during the medical procedure, and wherein the second device comprises at least one connector device that communicates with the opening when the second device is aligned with the port means, by which a connection can be made with the reservoir to use the reservoir after the medical procedure.

9. The apparatus according to claim 8 wherein the port means comprises a plurality of openings in the reservoir, and wherein at least one of the first and second devices comprises a plurality of connectors, each communicating with one of the openings when its respective device is aligned with the port means, to allow separate connections to be made to the reservoir.

10. The apparatus according to claim 7 wherein the first and second devices are releasably connected together so that they move together.

11. The apparatus according to claim 7 further comprising means for releasably locking the first and second devices in position when each is aligned with the port means.

12. The apparatus according to claim 11 wherein the means for releasably locking the first and second devices comprises a push button operable between an extended position in which the push button engages the first and second devices, and a depressed position in which the push button does not engage the first and second devices.

13. The apparatus according to claim 7 wherein the first and second devices are slidably mounted on the reservoir.

14. The apparatus according to claim 13 wherein the mounting means comprises opposing tracks between which the first and second devices are slidably mounted.

15. The apparatus according to claim 14 wherein the mounting means comprises a generally U-shaped track with the second device positioned between the legs of the "U" adjacent the closed end, and the first device positioned between the legs of the "U" adjacent the open end.

16. The apparatus according to claim 7 wherein the reservoir is divided into at least two chambers, wherein the port means comprises a vent hole communicating with each chamber; and wherein one of the first and second devices comprises means for closing the vent holes and the other of the first and second devices comprises means for connecting the vent holes.

17. The apparatus according to claim 6 in which the devices are releasably connected together in such a way that the port means is not uncovered as the primary device is moved out of alignment with the port means and the secondary device is moved into alignment with the port means.

18. The apparatus according to claim 10 in which the devices are releasably connected together in such a way that the port means is not uncovered as the first device is moved out of alignment with the port means and the second device is moved into alignment with the port means.

19. An apparatus for handling a patient's blood during a medical procedure which is convertible for use in blood collection after the procedure, the apparatus comprising:

a reservoir;

first port means in the reservoir comprising at least one opening;

a first device alignable with the first port means for adapting the reservoir for use during the procedure;

a second device alignable with the first port means for adapting the reservoir for use after the procedure;

first mounting means for mounting the first and second devices on the reservoir with the first means initially aligned with the port means to allow the reservoir to be used during the medical procedure, the mounting means allowing the first device to be moved out of the alignment with the port means and the second device to be moved into alignment with the port means to allow the reservoir to be used after the medical procedure;

second port means in the reservoir comprising at least one opening;

a third device alignable with the second port means for adapting the reservoir for use during the procedure;

a fourth device alignable with the second port means for adapting the reservoir for use after the procedure; and second mounting means for mounting the third and fourth devices on the reservoir with the third device initially aligned with the second port means to allow the reservoir to be used during the medical procedure, the mounting means allowing the third device to be moved out of the alignment with the second port means and the fourth device to be moved into alignment with the second port means to allow the reservoir to be used after the medical procedure.

20. The apparatus according to claim 19 wherein the first device comprises at least one connector that communicates with an opening of the first port means when the first device is aligned with the first port means, by which a connection can be made with the reservoir to use the reservoir during the medical procedure, and wherein the second device comprises at least one connector device that communicates with an opening of the first port means when the second means is aligned with the first port means, by which a connection can be made with the reservoir to use the reservoir after the medical procedure.

21. The apparatus according to claim 19 wherein the third device comprises at least one connector that communicates with an opening of the second port means when the third device is aligned with the second port means, by which a connection can be made with the reservoir to use the reservoir during the medical procedure, and wherein the fourth device comprises means for closing the second port means when the fourth device is aligned with the second port means to use the reservoir after the medical procedure.

22. The apparatus according to claim 19 wherein at least one of the port means comprises a plurality of openings in the reservoir, and wherein at least one of the means alignable with that port means comprises a plurality of connector devices, each communicating with one of the openings when aligned with the port means, to allow separate connections to be made to the reservoir.

23. The apparatus according to claim 19 further comprising means for releasably interlocking the first and second devices so that the first and second devices move together, and means for releasably interlocking the third and fourth devices so that the third and fourth devices move together.

24. The apparatus according to claim 19 further comprising means for releasably locking the first and second devices in position when each is aligned with the first port means, and means for releasably locking the third and fourth devices in position when each is aligned with the second port means.

25. The apparatus according to claim 19 wherein the first and second devices are slidably mounted on the reservoir, and wherein the third and fourth devices are slidably mounted on the reservoir.

26. The apparatus according to claim 25 wherein the first mounting means comprises opposing tracks between which the first and second devices are slidably mounted and wherein the second mounting means comprises opposing tracks between which the third and fourth devices are slidably mounted.

27. The apparatus according to claim 26 wherein the first mounting means comprises a first generally U-shaped track with the second device positioned between the legs of the "U" adjacent the closed end, and the first device positioned between the legs of the "U" adjacent the open end, and wherein the second mounting means comprises a second generally U-shaped track with the fourth device positioned between the legs of the "U" adjacent the closed end, and the third means positioned between the legs of the "U" adjacent the open end.

28. The apparatus according to claim 27 wherein the first and second U-shaped tracks are positioned side-by-side on the reservoir.

29. The apparatus according to claim 27 further second device and the third and fourth device in alignment with their respective port means.

30. The apparatus according to claim 29 wherein the releasable locking means comprises a push button operable between an extended position in which the button engages the device aligned with the first and the second port means, and a depressed position in which the button does not engage the device aligned with the first and the second port means.

31. The apparatus according to claim 19 wherein the reservoir is divided into at least two chambers, wherein at least one of the first and second port means comprises a vent hole communicating with each chamber; and wherein one of the devices alignable with the port means comprises means for closing the vent holes and the other of the devices alignable with the port means comprises means for connecting the vent holes.

32. A cardiotomy autotransfusion apparatus for use during surgery that is convertible to a blood collection device for use after surgery, the apparatus comprising:

a reservoir;

a first port means in the reservoir comprising at least one opening;

a first block, alignable with the first port means, comprising at least one connector device that communicates with an opening of the first port means when the first block is aligned with the first port means, by which a connection can be made with the reservoir to use the reservoir during surgery;

a second block, alignable with the first port means, comprising at least one connector device that communicates with an opening of the first port means when the second block is aligned with the first port means, by which a connection can be made with the reservoir to use the reservoir after surgery;

a first mounting means for mounting the first and second blocks on the reservoir with the first block initially aligned with the first port means to allow the reservoir to be used during surgery, the first mounting means allowing the first block to be moved out of the alignment with the first port means and the second block to be moved into alignment with the first port means to allow the reservoir to be used after surgery;

second port means in the reservoir comprising at least one opening;

a third block, alignable with the second port means, comprising at least one connector device that communicates with an opening of the second port means when the third block is aligned with the second port means, by which a connection can be made with the reservoir to use the reservoir during surgery;

a fourth block, alignable with the second port means, for closing the second port means when the fourth block is aligned with the second port means, to use the reservoir after surgery;

second mounting means for mounting the third and fourth blocks on the reservoir with the third block initially aligned with the second port means to allow the reservoir to be used during surgery, the second mounting means allowing the third block to be moved out of the alignment with the second port means and the fourth block to be moved into alignment with the second port means to allow the reservoir to be used after surgery.

33. The apparatus according to claim 32 wherein at least one of the port means comprises a plurality of openings in the reservoir, and wherein at least one of the blocks alignable with that port means comprises a plurality of connector devices, each communicating with one of the openings when its respective block is aligned with the port means, to allow separate connections to be made to the reservoir.

34. The apparatus according to claim 32 further comprising means for releasably interlocking the first and second blocks so that the first and second blocks move together, and means for releasably interlocking the third and fourth blocks so that the third and fourth means move together.

35. The apparatus according to claim 32 further comprising means for releasably locking the first and second blocks in position when each is aligned with the first port means, and means for releasably locking the third and fourth blocks in position when each is aligned with the second port means.

36. The apparatus according to claim 32 wherein the first and second blocks are slidably mounted on the reservoir, and wherein the third and fourth blocks are slidably mounted on the reservoir.

37. The apparatus according to claim 36 wherein the first mounting means comprises opposing tracks between which the first and second blocks are slidably mounted and wherein the second mounting means comprises opposing tracks between which the third and fourth blocks are slidably mounted.

38. The apparatus according to claim 36 wherein the first mounting means comprises a first generally U-shaped track with the second block positioned between the legs of the "U" adjacent the closed end, and the first block positioned between the legs of the "U" adjacent the open end, and wherein the second mounting means comprises a second generally U-shaped track with the fourth block positioned between the legs of the "U" adjacent the closed end, and the third block positioned between the legs of the "U" adjacent the open end.

39. The apparatus according to claim 38 wherein the first and second U-shaped tracks are positioned side-by-side on the reservoir.

40. The apparatus according to claim 39 further comprising means for releasably locking the first and second means and the third and fourth means in alignment with their respective port means.

41. The apparatus according to claim 40 wherein the releasable locking means comprises a push button operable between an extended position in which the button engages the blocks aligned with the first and the second port means, and a depressed position in which the button does not engage the blocks aligned with the first and the second port means.

42. An apparatus for handling a patient's blood during a medical procedure, the apparatus comprising:
a reservoir;
port means in the reservoir comprising at least one opening;
a device alignable with the port means to which connections can be made for adapting the reservoir for use during the medical procedure;
a cover, separate from the first device, alignable with the port means, for closing the port means after the medical procedure; and
mounting means for mounting the device and the cover on the reservoir with the device initially aligned with the port means to allow the reservoir to be used during the medical procedure, the mounting means allowing the device to be moved out of alignment with the port means and removed from the reservoir, and allowing the cover to be moved into alignment with the port means to close the reservoir after the medical procedure.

* * * * *

UNITED STATES PATENT AND TRADEMARK OFFICE
CERTIFICATE OF CORRECTION

PATENT NO. : 5,149,318
DATED : September 22, 1992
INVENTOR(S) : Erin J. Lindsay

It is certified that error appears in the above-indentified patent and that said Letters Patent is hereby corrected as shown below:

Column 13, Line 50, before the word alignment, delete "the".

Column 16, Line 22, change "27" to --28--.

Column 16, Line 22, after the word further and before the word second, insert --comprising means for releasably locking the first and--.

Signed and Sealed this

Fourteenth Day of September, 1993

Attest:

BRUCE LEHMAN

*Attesting Officer*     *Commissioner of Patents and Trademarks*